United States Patent [19]

Wright et al.

[11] 4,121,035

[45] Oct. 17, 1978

[54] 5-AMINO-2-HYDRAZINOPYRIDINE AND DERIVATIVES THEREOF

[75] Inventors: George C. Wright, Norwich; James L. Butterfield, New Berlin, both of N.Y.

[73] Assignee: Morton-Norwich Products, Inc., Norwich, N.Y.

[21] Appl. No.: 770,507

[22] Filed: Feb. 22, 1977

[51] Int. Cl.$^2$ .................... C07D 213/77; A61K 31/44
[52] U.S. Cl. ............................... 542/417; 260/296 R; 424/263
[58] Field of Search .................... 542/417; 260/296 R, 260/240 G

[56] References Cited
PUBLICATIONS

Bernstein et al., J. American Chem. Soc. 69, 1151–1158 (1947).
Sommer, L., Chem. Abst., vol. 79, No. 19–21, 1973, parag. 121493c.
Bell et al., Chem. Abst., vol. 70, 1969, parag. 87484c.

Primary Examiner—Henry R. Jiles
Assistant Examiner—Cary Owens
Attorney, Agent, or Firm—Anthony J. Franze

[57] ABSTRACT

5-Amino-2-hydrazinopyridine and derivatives thereof are useful as antihypertensive agents.

4 Claims, No Drawings

5-AMINO-2-HYDRAZINOPYRIDINE AND DERIVATIVES THEREOF

This invention is concerned with chemical compounds. In particular, it is concerned with chemical compounds of the formula:

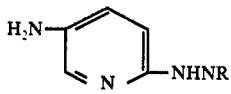

wherein R is $H_2$, benzylidene or 3,4-dimethoxybenzylidene and their hydrochloride salts.

The compounds of this invention possess pharmacological activity. They are capable when administered to hypertensive animals in less than toxic dose of reducing arterial blood pressure. The antihypertensive ability of the compounds of this invention is demonstrated by their intraperitoneal administration in a dose of about 50 mg/kg dispersed in distilled water to unanesthetized, spontaneously hypertensive rats whereupon arterial blood pressure is reduced.

The compounds of this invention are readily formulated in conventional pharmaceutical dosage forms such as tablets, elixires, suspensions, capsules and the like employing known excipients and adjuvants.

In order that this invention may be readily available to and understood by those skilled in the art, the following illustrative examples are supplied.

EXAMPLE I

5-Amino-2-hydrazinopyridine Dihydrochloride

A mixture of 2-hydrazino-5-nitropyridine (6.0 g, 0.039 mole) methanol (130 ml), and 5% Pd/C (50% $H_2O$) (0.6 g) was subjected to hydrogenation over 1.4 hours. A pressure drop of 80% of theory was observed. The reaction mixture was filtered, cooled in an ice bath, and immediately treated with a solution of dry HCL-isopropanol (30 ml) to a pH of 1. The resulting crystalline product was collected by filtration and washed with ethanol (5 × 10 ml), ether; m.p. 174°–176° dec., yield: 5.1 g (66%).

Anal. Calcd. as $C_5H_8H_4.2HCL$: C, 30.47; H, 5.11; N, 28.43. Found: C, 30.68; H, 5.24; N, 28.71.

EXAMPLE II

Veratraldehyde 5-Amino-2-pyridylhydrazone Dihydrochloride

A solution of 5.0 g (0.025 mole) of the compound of Example I in a mixture of 13 ml of $H_2O$ and 20 ml of $CH_3OH$ was treated rapidly with a solution of 4.7 g (0.027 mole) of veratraldehyde in 40 ml of methanol using mechanical stirring. The reaction mixture was stirred rapidly for 0.8 hr and filtered. The yellow-brown solid was washed with 40 ml of methanol, ether and air dried, m.p. 232°–233°dec. yield: 7.2 g (83%). Recrystallization from methanol raised the melting point to 235°–236°, dec.

Anal. Calcd. for $C_{14}H_{16}N_4O_2.2HCL$: C, 48.70; H, 5.26; N, 15.83. Found: C, 48.79; H, 5.43; N, 15.83.

EXAMPLE III

Benzaldehyde 5-Amino-2-pyridylhydrazone Hydrochloride Hemihydrate

A solution of 15.0 g (0.076 mole) of the compound of Example I in a mixture of 55 ml of $H_2O$ and 30 ml of $CH_3OH$ was treated rapidly with a solution of 9 g (0.077 mole) of benzaldehyde in 55 ml of methanol using mechanical stirring. The reaction mixture was stirred for 1.5 hrs and filtered. The pale yellow solid was washed with 30 ml of methanol, ether and air dried, m.p. 210° soften, 216°–220° dec, yield: 6.5 g (34%).

The above mother liquor on cooling gave an additional 10.0 g (51%) of the product, m.p. 191°–198° dec.

The crude products were combined and recrystallized from 675 ml of methanol. The yellow compound was washed with methanol, ether and air dried, m.p. 216°–220° dec, yield: 3 g (15%).

Anal. Calcd. for $C_{12}H_{12}N_4.HCL$. ½ HO: C, 55.92; H, 5.48; N, 21.91. Found: C, 56.05; H, 5.48; N, 21.91.

What is claimed is:

1. A compound of the formula:

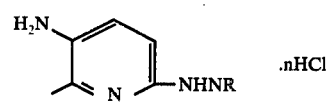

wherein R is $H_2$, benzylidene or 3,4-dimethoxybenzylidene and $n$ is 1 or 2.

2. The compound 5-amino-2-hydrazinopyridine dihydrochloride.

3. The compound veratraldehyde 5-amino-2-pyridylhydrazone dihydrochloride.

4. The compound benzaldehyde 5-amino-2-pyridylhydrazone hydrochloride.